United States Patent [19]

Johnson, Jr.

[11] Plant 5,071

[45] Jul. 19, 1983

[54] STRAWBERRY PLANT

[75] Inventor: Harold A. Johnson, Jr., Watsonville, Calif.

[73] Assignee: Driscoll Strawberry Associates, Inc., Watsonville, Calif.

[21] Appl. No.: 338,774

[22] Filed: Jan. 11, 1982

[51] Int. Cl.[3] ..... A01H 5/03

[52] U.S. Cl. ..... Plt./48

[58] Field of Search ..... Plt./48

*Primary Examiner*—Robert E. Bagwill

*Attorney, Agent, or Firm*—Townsend & Townsend

[57] ABSTRACT

A new distinct spring bearing variety of strawberry plant characterized by its large volume of fruit production in late April and early May and continued production through June. The variety is particularly distinguished by its lack of tertiary fruit in May and consistent maintenance of large fruit size making it a variety of high total yield. A conspicuous light colored band around the calyx is characteristic of the berries which, in shape, are short to medium conic, to short to medium wedge. The plant is a vigorous and abundant runner producer at the nursery and the fruit has good color, flavor and a typical strawberry aroma which provides excellent dessert quality.

1 Drawing Figure

1

This invention relates to a new and distinct variety of strawberry selected as J2 and now known as the Thomas and which is a result of a cross of the unpatented variety known as the Driscoll Strawberry Associates Selection G7 and the unpatented variety the Driscoll Strawberry Associates Selection G8.

The seedlings resulting from the aforementioned cross were grown and asexually multiplied in Shasta County, Calif., and tested in the fruiting beds on the property of member growers of Driscoll Strawberry Association, Inc. Clones of the seedlings were also held at the Propagation Nursery in Shasta County. One plant was selected from the aforementioned group of seedlings and further asexually reproduced by runners in the Shasta County Nursery of Driscoll Strawberry Associates, Inc. Tests followed in various parts of California during intervening seasons on various properties of grower members of the Driscoll Strawberry Associates, Inc. These tests indicated the merits of the novel plant and resulted in its selection as a promising test variety.

In the drawings:

FIG. 1 of the accompanying drawing illustrates plant parts of the new variety, typical in size, shape and color. A berry in cross section illustrates flesh color and characteristic core cavity. The inflorescence pictured illustrates typical branching and relative size during May. The pedicel holding the primary berry originates mainly at the axil union of two long pedicels with the two secondary berries developing farther from the axil than the primary. In this inflorescence there are only three berries, which is common during this time of year, but five or more is not uncommon. The drawing shows two flowers, one exposing the petals and one exposing the calyx. The one exposing the petals shows anthers with an abundance of pollen and overlapping petals. The calyx view illustrates sepals with a minimum of overlapping. The mature leaf is typical in color and the way the leaflets would be held on the plant. Younger leaflets would be cupped upward uniformly from the central leaflet vein and would be lighter in color. The petiole is free of bracts. The petiolule of the central leaflet is conspicuous and is typical.

This novel new summer planted, spring variety is adapted mainly to the central coast of California, and

2 even though it is not considered an early variety, it produces a large volume in late April and early May and with continuous production through June. It has some value as a winter planted variety in Oxnard, Calif., with production startng in late March.

When summer planted in Watsonville it produces a strong plant and in the spring following a summer planting the plant is larger than H4—U.S. Plant Pat. No. 3,987. However, the plant is not considered dense. The leaflets are larger than H4 and are lighter in color. There is a considerable darkening from young to mature leaflets. The serrations on the new variety are more distinct and are sharper at the apex than H4. The inflorescence of the new variety is long, longer than H4. In later April and May many berries originate from a single pedicel coming from the crown.

Many of the subsequent berries are produced on a inflorescence with one primary and two secondaries. This lack of tertiary fruit during May helps maintain consistent fruit size. Under Watsonville conditions the new variety peaks at the same time as H4, but the fruit size is greater on the new variety, giving more total yield. The fruit color of J2 is lighter than H4 and is slow to darken when left on the vine after the normal picking date. Also, the first primary berries in the spring are not as irregularly shaped as H4, even though there is some irregularity present in the fruit of J2. Individual sepals on H4 are wider, more conspicuous and there is more over-lapping. J2 produces many berries with a conspicuous light colored band around the calyx without seed, but within this band there may be a few isolated seed present. This seed develops on top of exerted fleshy growth. The pedicel and portions of the calyx are prone to reddening at various times of the year and may or may not be associated with a leafspot. The firmness of the skin and flesh of the new variety is good, equal to H4, even though it doesn't appear as firm to the touch as H4. The seed of the new variety doesn't become exerted as H4. The flavor is good and has been judged by panels to be superior to H4. The fruit of the new variety has a typical strawberry aroma, more noticeable than H4.

Early testing has shown that the two-spotted spider mite will be slower to build in large numbers per leaflet than other varieties in the tests, as well as being relatively tolerant to Botrytis infection after a rain. J2 is considered a good runner producer at the nursery. J2 has not been tested against the Verticillium wilt pathogen. As a seedling and selection, this new variety withstood the natural invasions of certain virus components found in Central and Southern California without losing its ability to produce. Under early spring conditions plants may be susceptible to Mycospharella Leafspot. It appears to be tolerant of Powdery Mildew.

The varietal characteristics of the novel plant, described below in detail, were observed mainly during May, in the Watsonville area of California, which is a cool coastal area near the Pacific Ocean. The drawing was taken in Watsonville on May 19, and specific measurements were also made in May. The color terminology is in accordance with Muncell Color System.

*Plant.*—Medium to large, vigorous if given proper nutrients. It has an extensive root system.

*Leaves.*—Mostly large in size, central leaflet average 8 to 10 cm. in width and length, but may vary, depending on the environment and time of year. Petiole length also varies, but is considered long. Petiolules of central leaflets are considered medium to long, 8 to 12 mm. Serrations at leaflet margins are medium deep, abundant, ovate with an acute apex, often double. Bracts are not normally present on the petiole. Leaflet surface is mildly rugose and young leaflets are mostly cupped upward from the center of the veins to the leaflet margin. The color of the upper side of the leaflet when mature is 5.6GY 2.3/3.6. Isozymes in leaf extracts.

Phosphoglucoisomerase (PGI) 5 banded identical to 'Shasta' designates "A5".

Leucine amino peptidase (LAP) single banded, identical to 'Shasta' — designated "B1" or 3 banded — designated "B4".

Phosphoglucomutase (PGM) 5 banded, identical to 'Shasta' designated "C4".

This testing done by University of California according to a procedure described in publication: "Electrophoretic characterization of California strawberry cultivars"— by Bringhurst 1981.

| | | PGI | LAP | PGM |
|---|---|---|---|---|
| Summarizing | J2 Variety | A5 | B1 or B4 | C4 |
| And Compared with H4 | H4 Variety | A3 | B3 | C2 |

*Runners.*—Runners are vigorous and abundant at the nursery and after being summer planted in the fruiting bed. May also produce some runners in the summer, in the following year after being summer planted.

*Inflorescence.*—Considered long, many over 30 cm. in length with a common peduncle varying considerably in length, but pedicels mostly long. Early spring fruit often come from a single pedicel from the crown. Subsequent fruit often are borne on pedicels that originate from a common peduncle without secondary peduncles present. The pedicel holding the primary berry originates mostly from the axil of secondary peduncles or pedicels that hold secondary berries. Secondary berries often develop at a greater distance from the common peduncle than the primary. The pedicels are considered small in diameter and often become reddish in color. The hair on pedicels 20 mm. from the calyx is held irregularly perpendicular to the pedicel. The flowers are generally visible above the plant and primary flowers are large and showy with petals that over-lap. Anthers produce an abundance of pollen.

*Fruit.*—The fruit size in the spring following a summer planting is considered large with only a slight difference between primaries and secondaries, but tertiaries may be smaller. Primaries are mostly 40 to 45 mm. in width and length. The shape is mainly short to medium conic to short to medium wedge, as described in the USDA Bulletin 1043. The shoulders are rounded, not necked, but may have a white band around the calyx that is void of seed except a few conspicuous seed. These seed give the surface in the band area a blistered appearance as the flesh surrounding the few seed that do form are exerted on the fruit surface. The fruit surface has a minimum of roughness and longitudinal ribs, but the surface isn't completely smooth when observing the complete surface. The seed is medium in size and yellow, but darkens easily when exposed to full sun.

The seed is generally held equal to the fruit surface, but may be slightly inserted to slightly exerted. The flesh and skin surface is considered firm. The core is medium in size. The dessert quality is considered good. Color of the fruit is 6.6R — 2.9/9.7 and the flesh color near the epidermis is 6.9R—4.1/16.1. The surface color tends to hold its color without excessively darkening if picking is delayed or the fruit is held out of storage longer than normal. Less than a percentage of fruit have a dark streak extending longitudinally on the fruit surface.

*Calyx.*—Diameter is medium to large, but individual sepals are elliptical to lanceolate and acute, not considered broad, with a minimum of overlap and a minimum of serrations. The calyx is mostly slightly reflexed and attached to the fruit in a basin below the outline of the fruit when viewing a berry from the side. Color of sepals on side facing the berry is 1.5G — 2.8/7.4.

I claim:

1. The new and distinct strawberry plant herein described and illustrated, and identified by the characteristics enumerated above.

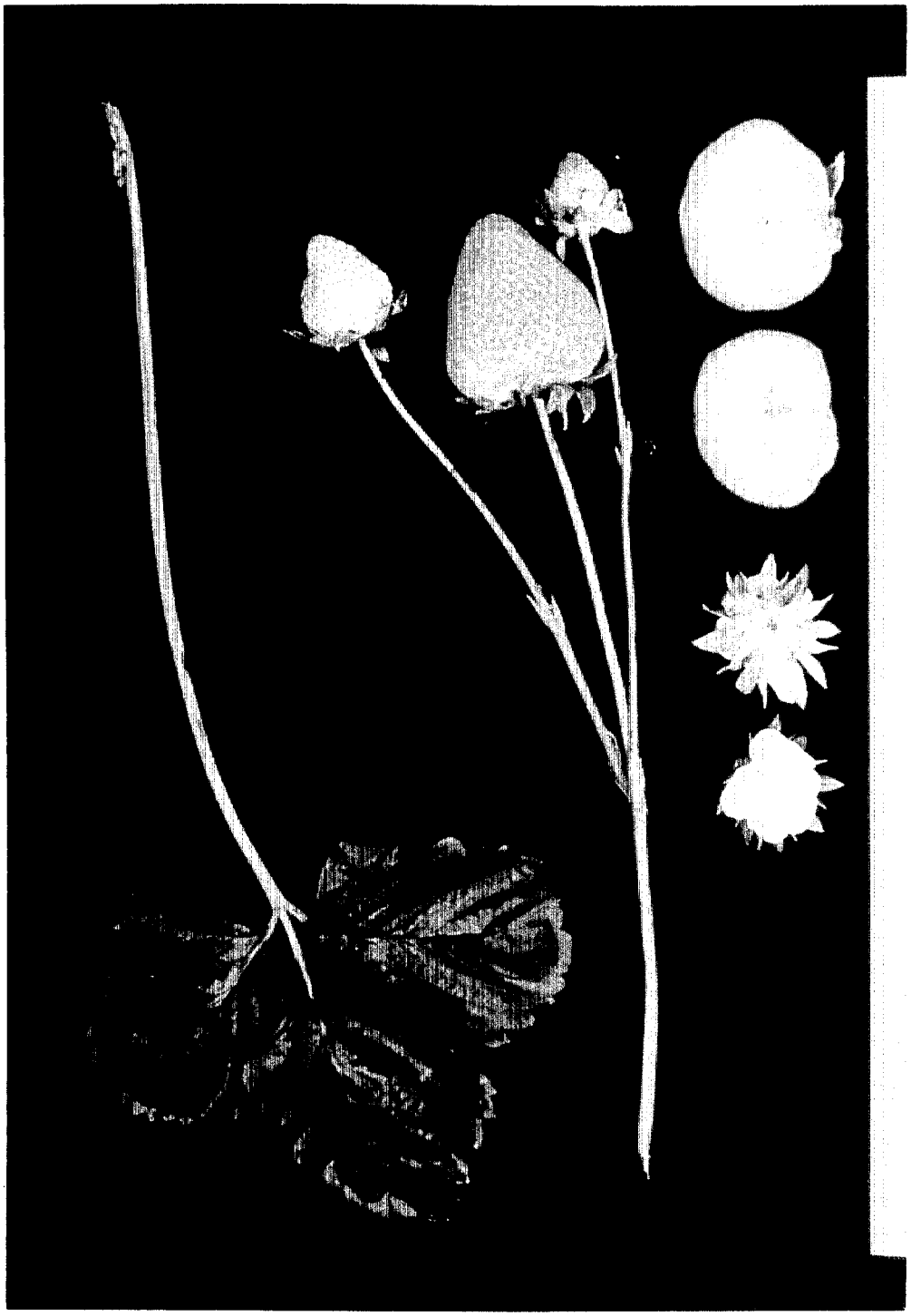

* * * * *